United States Patent [19]

Yu

[11] 4,124,370
[45] Nov. 7, 1978

[54] DIPHENYL ETHERS FOR TOBACCO SUCKER CONTROL

[75] Inventor: Pyung K. Yu, Doylestown, Pa.

[73] Assignee: Rohm and Haas Company, Philadelphia, Pa.

[21] Appl. No.: 575,666

[22] Filed: May 8, 1975

[51] Int. Cl.² .............................................. A01N 5/00
[52] U.S. Cl. ........................................................ 71/78
[58] Field of Search .................................... 71/78, 124

[56] References Cited

U.S. PATENT DOCUMENTS

| 3,322,525 | 5/1967 | Martin et al. ........................... 71/124 |
| 3,427,146 | 2/1969 | Tamura et al. ............................. 71/78 |
| 3,798,276 | 3/1974 | Bayer et al. ......................... 71/124 X |
| 3,849,503 | 11/1974 | Shigehara et al. ................. 71/124 X |
| 3,852,057 | 12/1974 | Findley et al. ........................... 71/78 |
| 3,888,932 | 6/1975 | Bayer et al. ........................ 71/124 X |

OTHER PUBLICATIONS

Fr. Pat. 1,394,558, Chem. Abst., vol. 63 (1965) 14771g.
Reith, Chem. Abst., vol. 59 (1963) 2556f.
Fr. Pat. 1,549,827, Chem. Abst., vol. 72 (1970) 43129c.
Engelsman et al., vol. 57 (1962) 374h, Chem. Abst.
Neth. appl. 6,512,264, Chem. Abst., vol. 65, (1966) 10530f.

*Primary Examiner*—Catherine L. Mills

[57] ABSTRACT

Diphenyl ethers having the formula

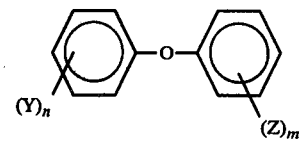

where
Y and Z are halogen, alkyl, trifluoromethyl, alkoxy, hydroxy, nitro, cyano, carboxy, carbalkoxy, carbamoyl, or alkylthio, and
$m$ and $n$ are 0, 1, 2, or 3, are useful in controlling undesirable secondary growth in plants, particularly sucker growth in tobacco.

13 Claims, No Drawings

DIPHENYL ETHERS FOR TOBACCO SUCKER CONTROL

CROSS REFERENCE TO RELATED APPLICATION

This application is related to my copending application Ser. No. 575,667, entitled "Diphenyl Sulfides for Tobacco Sucker Control", filed on even date herewith and assigned to common assignee, now abandoned.

This invention relates to plant growth control, and more particularly to control of the undesirable growth of suckers in tobacco plants.

Various plants, including tobacco and tomato, are sujbect to various forms of undesirable secondary growth. For example, in tobacco, the growth of suckers, that is axillary buds, not only detracts from the growth of the tobacco leaves, but also has a deleterious effect on the quality of the tobacco produced from the leaves. Manual removal of these suckers is both time-consuming and expensive. Furthermore, the chemicals heretofore employed in removing these suckers have been generally either too expensive or too subject to side effects.

It has now been found that sucker growth in tobacco plants can be controlled by applying to the growing plants a diphenyl sulfide or a diphenyl ether. Generally, the compounds which are useful in inhibiting tobacco sucker growth have the formula

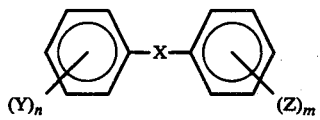

wherein
X is an oxygen atom or a sulfur atom;
each Y independently is a halogen atom, preferably chlorine or bromine, an alkyl group, preferably having up to 8 carbon atoms, a trifluoromethyl group, an alkoxy group, preferably having up to 4 carbon atoms, a hydroxy group, a nitro group, a cyano group, a carboxy group, a carbalkoxy group, preferably having up to 4 carbon atoms in the alkoxy moiety, a carbamoyl group, an alkyl or dialkyl carbamoyl group, preferably having up to 4 carbon atoms in the alkyl groups, or an alkylthio group, preferably having up to 4 carbon atoms;
each Z independently is a halogen atom, preferably chlorine or bromine, an alkyl group, preferably having up to 8 carbon atoms, a trifluoromethyl group, an alkoxy group, preferably having up to 4 carbon atoms, a hydroxy group, a nitro group, a cyano group, a carboxy group, or a carbalkoxy group, preferably having up to 4 carbon atoms on the alkoxy moiety, a carbamoyl group, an alkyl or dialkyl carbamoyl group, preferably having up to 4 carbon atoms in the alkyl groups, or an alkylthio group, preferably having up to 4 carbon atoms;
$m$ is 0, 1, 2, or 3, preferably 0 or 1; and
$n$ is 0, 1, 2, or 3, preferably 1 or 2.

A preferred group of diphenyl sulfides and diphenyl ethers which are useful in the present invention are those in which the Y and Z substituents are halogen, alkyl, trifluoromethyl, or alkoxy, and those in which $n$ is 1 (preferably at the 3-position) and $m$ is 0. The most preferred compounds are those in which Y is a methyl group or a chlorine atom, $n$ is 1, and $m$ is 0.

Generally, the compounds used in the present invention are applied to the tobacco plants during the topping stage, and are usually applied during the period of about 1 to 3 days before to about 1 to 3 days after topping, and preferably on the same day as topping. The compounds can be applied in any amount which will give the desired degree of control of sucker growth, without significantly adversely affecting the growth of the tobacco plants. Typical rates of application will be from about 0.5 to about 20 pounds per acre, and preferably about 1 to about 10 pounds per acre.

The compounds of the invention can be applied to the growth medium or to plants to be treated either by itself or, as is generally done, as a component in an agricultural composition or formulation which also comprises an agronomically acceptable carrier. By agronomically acceptable carrier is meant any substance which can be used to dissolve, disperse, or diffuse a compound in the composition without impairing the effectiveness of the compound and which by itself has no detrimental effect on the soil, equipment, crops, or agronomic environment. Mixtures of the compounds of the invention may also be used in any of these formulations. The compositions of the invention can be either solid or liquid formulations or solutions. For examples, the compounds can be formulated as wettable powders, emulsifiable concentrates, or flowable emulsion concentrates. In such formulations, the compounds are extended with a liquid or solid carrier and, when desired, suitable surfactants are incorporated.

It is usually desirable, particularly in post-emergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 25% to about 75%.

For the preparation of emulsifiable concentrates, the compounds can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols, such as t-octylphenol, or long-chain alcohols, and their phosphoric acid esters, mercaptans, carboxylic acids, and reactive amines and partially esterified polyhydric alcohols. Solvent, soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water soluble salt of a polyacrylic acid. The concentration of the active ingredient in emulsifiable concentrates is usually about 10% to 60% by weight and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent can constitute about 0.5% to about 3% of the composition, and a wetting agent can constitute from about 0.1% to about 5% of the composition.

The compounds of the invention can be applied as sprays by methods commonly employed, such as conventional high-gallonage hydraulic sprays, low gallonage sprays, air-blast sprays and aerial sprays. For low volume applications a solution of the compound is usually used. The dilution and rate of application will usually depend upon such factors as the type of equipment employed, the method of application, and the area to be treated.

For some applications, it may be desirable to use one or more other tobacco sucker control agents along with compounds of the invention. Examples of other tobacco sucker control agents which can be combined or applied sequentially with the compounds of the invention to provide additional advantages and effectiveness include maleic hydrazide, N-2-pentyl-3,4-dimethyl-2,6-dinitroaniline, dodecyl dimethyl ammonium acetate, 5,6-dihydro-2,3-diphenyl-1,4-oxathiin, N-n-butyl-N-ethyl-2,6-dinitro-4-trifluoromethylaniline, $C_6$ to $C_{12}$ fatty alcohols, and mixtures of such alchols, and the like. When mixtures of tobacco sucker control agents are employed, the relative proportions which are used can be varied greatly depending on the degree of control desired and particular conditions which may be present. The compounds of the invention can also be combined when appropriate with other presticides useful in tobacco, including insecticides, fungicides, viricides, herbicides, and the like, to simplify application of these materials.

The compounds of the invention or their precursors are either known compounds or can be prepared by conventional synthetic methods. For example, the diphenyl sulfides of the invention can be prepared by reacting a copper or alkali metal salt of a suitable thiophenol with a suitable aryl halide, and the diphenyl ethers of the invention can be prepared by reacting an alkali metal salt of a suitable phenol with a suitable aryl halide, generally in the presence of a base. Other conventional methods and modifications of these methods can also be employed in preparing compounds of the invention.

The following examples will further illustrate this invention, but are not intended to limit it in any way. Examples 6, 31, and 35 show typical procedures used in preparing the diphenyl sulfides of the invention. Examples 38 and 42 show typical procedures used in preparing the diphenyl ethers of the invention. All parts and percentages are by weight and all temperatues in degrees Centigrade unless otherwise noted.

EXAMPLE 6

Preparation of 4-Methyldiphenyl sulfide

To a three-necked flask equipped with a good mechanical stirrer and an air condenser is added 31.1g (0.18 moles) of copper (I) thiophenolate, 25.7g (0.15 moles) of 4-bromotoluene, 135 ml of quinoline, and 13.5 ml of pyridine. The resultant mixture is slowly heated to reflux (200°) and maintained at this temperature for 5 hours longer than is necessary to obtain a homogeneous solution. Upon cooling to 25°, the solution is poured into 1200 ml of a 3.0 M hydrochloric acid solution. The transfer is facilitated by several 10 ml portions of pyridine. After allowing the acidified reaction mixture to set for several hours, the gummy, dark solid is collected by vacuum filtration and the crude product extracted from the copper salts with five 100-ml portions of ether. This is accomplished by treating the gummy solid with ether in a fritted glass funnel with thorough stirring and subsequent removal of the extract by vacuum filtration. The combined organic layers are washed with a 3.0 M hydrochloric acid solution, water, and a saturated sodium chloride solution, dried ($MgSO_4$) and concentrated in vacuo. Distillation at reduced pressure affords 25.3g (84%) of a pale yellow liquid, b(0.15 mm) 93.5°-94.5°. The pmr and ir spectra are compatible with the desired structure.

EXAMPLE 31

Preparation of 2-Chloro-4-(trifluoromethyl)-4'-methoxydiphenyl sulfide

To a stirred solution containing 14.0 g (0.1 mole) of 4-methoxybenzenethiol in 75 ml of dimethylforamide is added 6.6 g (0.1 mole) of 85% potassium hydroxide pellets under an atmosphere of nitrogen at 25°. The resultant yellow mixture is heated until all of the potassium hydroxide has dissolved, whereupon it is cooled to about 70° and 21.5 g (0.1 mole) of 3,4-dichloro-α,α,α-benzotrifluoride is added over a period of 20 min. The addition is accompanied by an immediate formation of potassium chloride. The suspension is heated at 120° to effect complete reaction, at which time it is cooled, diluted to a volume of 400 ml with water, and extracted with three portions of ether. The combined extracts are washed with a 5% sodium hydroxide solution, a 3-molar hydrochloric acid solution, water, and a saturated sodium chloride solution, dried (magnesium sulfate), and concentrated in vacuo. The resultant solid is recrystalized from methanol-water to afford 23.1 g (73%) of product as white crystals, mp 71.5°-74°. The pmr and ir spectra are compatible with the desired structure. An analytical sample is prepared by recrystalization from methanol, mp 74.5°-75°. Anal. Calc'd. for $C_{14}H_{10}F_3ClOS$: C, 52.75; H, 3.16; F, 17.88; Cl, 11.12; S, 10.06. Found: C, 52,67; H, 3.11; F, 17.95; Cl, 11.07; S, 10.30.

EXAMPLE 35

Preparation of 3-Bromo-4-Methyldiphenyl sulfide

To a solution containing 8.00 g (0.04 mole) of 4-methyldiphenyl sulfide in 140 ml of glacial acetic acid and 45 ml of water is added 8.63 g (0.02 mole) of 1,4-diazabicyclo[2.2.2]octanetetrabromide in one portion at 25°. The resultant mixture is slowly heated with addition of more solvents until attainment of a homogenous solution, at which time it is diluted with water and chilled at 0°. Filtration, followed by recrystallization from methanol effects isolation of 3.8 g (44%) of product as a white solid, mp 79°–81°. Spectral data is in agreement with the assigned structure. An analytical sample is prepared by recrystalization from methanol, mp 82°–83.5°. Anal. Calc'd. for $C_{13}H_{11}BrO$: C, 55.92; H, 3.97; Br, 28.62; S, 11.48. Found: C, 55.84; H, 4.03; Br, 27.67; S, 11.56.

EXAMPLE 38

Preparation of 3-Methyldiphenyl ether

A stirred mixture containing 12.0 g (0.082 mole) of dry potassium m-cresate, 0.3 g of copper-bronze, and 75 ml of bromobenzene is heated at reflux with concomitant monitoring of the progress of the reaction with vapor phase chromotograph techniques. When reaction is complete, the crude reaction mixture is cooled and treated with dilute hydrochloric acid (pH 1.0) and the copper-bronze recovered by filtration. The organic phase is then washed free of acid with water, dried (magnesium sulfate), and concentrated in vacuo. Distillation at reduced pressure affords 6.0 g (40%) of colorless liquid, b(0.2 mm) 68°–70°, whose spectral properties are compatible with the desired structure. This material is also prepared by reaction of potassium m-cresate with fluorobenzene in hot N-methyl-2-pyrrolidinone.

EXAMPLE 42

Preparation of 4-Chlorodiphenyl ether

A stirred solution containing 14.8 g (0.112 mole) of potassium phenoxide and 13.1 g (0.10 mole) of p-fluorochlorobenzene in 100 ml of N-methyl-2-pyrrolidinone is heated at reflux for a period of time necessary to effect complete reaction, as determined by vapor phase chromotography techniques. The crude reaction mixture is cooled and diluted to a volume of 400 ml with water, whereupon it is extracted with several portions of ether. The combined organic extracts are washed with a 5% sodium hydroxide solution, water, and a saturated sodium chloride solution, dried (magnesium sulfate), and concentrated in vacuo. Distillation at reduced pressure affords 11.1 g (54%) of material, b(0.05 mm) 73.5°–75.5°, whose spectral properties are in agreement with the desired structure.

The following Table I lists the structures of various representative diphenyl sulfides and diphenyl ethers which can be prepared using the above synthetic procedures or other known techniques.

TABLE 1

| Example No. | X | Z | Z' | Y | Y' |
|---|---|---|---|---|---|
| 1 | S | H | H | H | H |
| 2 | S | 4-OH | H | H | H |
| 3 | S | 3-CO₂H | H | H | H |
| 4 | S | 2-CH₃ | H | H | H |
| 5 | S | 3-CH₃ | H | H | H |
| 6 | S | 4-CH₃ | H | H | H |
| 7 | S | 2-Cl | H | H | H |
| 8 | S | 3-Cl | H | H | H |
| 9 | S | 4-Cl | H | H | H |
| 10 | S | 2-OCH₃ | H | H | H |
| 11 | S | 3-OCH₃ | H | H | H |
| 12 | S | 4-OCH₃ | H | H | H |
| 13 | S | 2-NO₂ | H | H | H |
| 14 | S | 3-NO₂ | H | H | H |
| 15 | S | 4-NO₂ | H | H | H |

TABLE 1-continued

| Example No. | X | Z | Z' | Y | Y' |
|---|---|---|---|---|---|
| 16 | S | 2-CF₃ | H | H | H |
| 17 | S | 3-CF₃ | H | H | H |
| 18 | S | 4-CF₃ | H | H | H |
| 19 | S | 2-CH₃ | H | 3-CF₃ | H |
| 20 | S | 3-CH₃ | H | 3-CF₃ | H |
| 21 | S | 4-CH₃ | H | 3-CF₃ | H |
| 22 | S | 2-Cl | H | 3-CF₃ | H |
| 23 | S | 3-Cl | H | 3-CF₃ | H |
| 24 | S | 4-Cl | H | 3-CF₃ | H |
| 25 | S | 2-CH₃ | H | 4-OCH₃ | H |
| 26 | S | 3-CH₃ | H | 4-OCH₃ | H |
| 27 | S | 4-CH₃ | H | 4-OCH₃ | H |
| 28 | S | 2-Cl | H | 4-OCH₃ | H |
| 29 | S | 3-Cl | H | 4-OCH₃ | H |
| 30 | S | 4-Cl | H | 4-OCH₃ | H |
| 31 | S | 2-Cl | 4-CF₃ | 4-OCH₃ | H |
| 32 | S | 4-NO₂ | H | 2-Cl | 4-CF₃ |
| 33 | S | 3-OCH₃ | 4-NO₂ | 2-Cl | 4-CF₃ |
| 34 | S | 3-CO₂CH₃ | 4-NO₂ | 2-Cl | 4-CF₃ |
| 35 | S | 3-Br | 4-CH₃ | H | H |
| 36 | S | 3-OCH₃ | 2-Br | H | H |
|  |  | 3-OCH₃ | 4-Br | H | H |
| 37 | O | H | H | 2-CH₃ | H |
| 38 | O | H | H | 3-CH₃ | H |
| 39 | O | H | H | 4-CH₃ | H |
| 40 | O | H | H | 2-Cl | H |
| 41 | O | H | H | 3-Cl | H |
| 42 | O | H | H | 4-Cl | H |
| 43 | O | H | H | 4-CF₃ | H |
| 44 | O | H | H | 2-Cl | 4-Cl |
| 45 | O | H | H | 2-COOH | H |
| 46 | O | H | H | 2-Cl | 4-CF₃ |
| 47 | O | 4-NO₂ | H | 3-CH₃ | H |
| 48 | O | 4-NO₂ | H | 2-NO₂ | 4-CF₃ |
| 49 | O | 3-OCH₂CH₃ | 4-NO₂ | 2-Cl | 4-CF₃ |
| 50 | O | 4-NO₂ | H | 2-Cl | 4-CF₃ |
| 51 | O | 4-NO₂ | H | 2-Cl | 4-Cl |
| 52 | O | 3-CO₂CH₃ | 4-NO₂ | 2-Cl | 4-Cl |
| 53 | O | 4-t-amyl | H | 4-NO₂ | H |
| 54 | O | 2-F | H | 4-NO₂ | H |
| 55 | O | 2-Cl | 4-CF₃ | 3-SC₂H₅ | 4-NO₂ |
| 56 | O | 2-Cl | 4-CF₃ | 4-CN | H |
| **57 | S | 2-OH | 3-Br 5-Cl | 2-OH | 3-Br 5-Cl |
| 58 | S | 2-OH | 3-Br 5-Cl | 2-OH | 3-Br 5-Cl |
| 59 | S | 2-OH | 5-Br | 2-OH | 5-Br |
| 60 | S | 4-OH | H | 4-OH | H |
| 61 | S | 2-OH | 5-t-octyl | 2-OH | 5-t-octyl |
| 62 | S | 3-CF₃ | H | 4-NO₂ | H |
| 63 | S | 4-OCH₃ | H | 4-NO₂ | H |
| 64 | O | 4-NO₂ | H | 2-Cl | H |
| 65 | O | 4-NO₂ | H | 3-Cl | H |
| 66 | O | 2-Cl | 4-Cl | 2-NO₂ | H |
| 67 | O | 2-Cl | 4-Cl | 4-Cl | H |

*50/50 mixture (by weight)
**diethylamine salt

The following diphenyl sulfides and diphenyl ethers representative of compounds which are useful in the practice of the present invention:

3-bromodiphenyl sulfide
3,3'-dibromodiphenyl sulfide
4-ethyldiphenyl sulfide
3,3'-dichlorodiphenyl sulfide
2-cyanodiphenyl sulfide
4-carbamoyldiphenyl sulfide
3-dimethylaminodiphenyl sulfide
4-carbethoxy-3'-methyldiphenylsulfide
2,4,6-trichlorodiphenyl sulfide
3,5-dichloro-3'-methyldiphenyl sulfide
3-n-butoxy-3'-chlorodiphenyl sulfide
2-cyano-4-trifluoromethyl-4'-nitrodiphenyl sulfide
3-bromodiphenyl ether
3-bromo-4'-chlorodiphenyl ether 3-carboxy-4-nitro-2',4'-dichlorodiphenyl ether
2-n-propyl-3'-chlorodiphenyl ether
3,3'-dichlorodiphenyl ether
3-chloro-3'-methyldiphenyl ether
4-ethoxydiphenyl ether
3-dimethylcarbamoyldiphenyl ether
2-hydroxy-3',5'-dichlorodiphenyl ether
3-trifluoromethyldiphenyl ether
3-chloro-4'-trifluoromethyldiphenyl ether
2,4-dichloro-6-fluorodiphenyl ether
3,4-dimethoxydiphenyl sulfide
3,3'-bis(trifluoromethyl)diphenyl sulfide
4,4'-dimethoxydiphenyl ether
4,4'-dimethoxydiphenyl sulfide
2,4'-dimethoxydiphenyl sulfide
4-methoxy-2'-nitrodiphenyl sulfide
3,4'-bis(trifluoromethyl)diphenyl sulfide
2,3'-bis(trifluoromethyl)diphenyl sulfide
3-nitro-3'-(trifluoromethyl)diphenyl sulfide
4-nitro-3'-(trifluoromethyl)diphenyl sulfide
2-nitro-3'-(trifluoromethyl)diphenyl sulfide
4-methoxy-3'-(trifluoromethyl)diphenyl sulfide
3-methoxy-3'-(trifluoromethyl)diphenyl sulfide
2-methoxy-3'-(trifluoromethyl)diphenyl sulfide
4-methoxy-4'-(trifluoromethyl)diphenyl sulfide
4-methoxy-2'-(trifluoromethyl)diphenyl sulfide
3,4'-dimethoxydiphenyl sulfide
3-nitro-4'-methoxydiphenyl sulfide

EXAMPLE 53

Control of Tobacco Suckers

This example shows the activity of diphenyl sulfides and diphenyl ethers in inhibiting the growth of tobacco suckers when compared to an untreated control. The following test procedure is employed. Tobacco plants growing in the greenhouse were topped at early flowering stage. Topping is necessary to induce increased growth of the remaining leaves by preventing development of the seed head and reducing the number of leaves on the plant. A few days after the topping, 150 milligrams of each compound was topically sprayed in 20 ml of acetone + water solution (85:15). The coarse spray, applied with no more than 20 lbs. pressure, was directed to the center of the plant so that it ran down the stalk and made contact with each sucker. A continual observation regarding phytotoxicity and degree of sucker killing was recorded. Final sucker control was determined 14 days after treatment by removing suckers from each plant and weighing them.

Table II summarizes typical results of these evaluations. The reduction in weight of tobacco suckers is the ratio of the weight of suckers on the treated plants to the weight of suckers on untreated control plants. Phytotoxicity ratings are based on a 0 to 5 scale, in which 0 represents no injury and 5 represents complete kill.

TABLE II

Control of Tobacco Sucker Growth

| Compound of Example No. | Rate (mg/plant) | % Reduction in Sucker Weight | Phyto-toxicity |
|---|---|---|---|
| 1 | 150 | 78.1 | 0 |
| 2 | 150 | 92.9 | 2 |
| 3 | 150 | 59.9 | 0 |
| 4 | 150 | 99.3 | 0 |
| 5 | 150 | 98.8 | 0 |
| 6 | 150 | 98.2 | 0 |
| 7 | 150 | 99.5 | 0 |
| 8 | 150 | 99.3 | 0 |
| 9 | 150 | 99.1 | 1 |
| 10 | 150 | 96.1 | 0 |
| 11 | 150 | 98.7 | 0 |

TABLE II-continued

Control of Tobacco Sucker Growth

| Compound of Example No. | Rate (mg/plant) | % Reduction in Sucker Weight | Phyto-toxicity |
|---|---|---|---|
| 12 | 150 | 95.0 | 0 |
| 13 | 150 | 85.9 | 1 |
| 14 | 150 | 98.2 | 2 |
| 15 | 150 | 99.0 | 3 |
| 16 | 150 | 99.3 | 0 |
| 17 | 150 | 99.9 | 0 |
| 18 | 150 | 80.7 | 0 |
| 19 | 150 | 89.0 | 0 |
| 20 | 150 | 94.7 | 0 |
| 21 | 150 | 99.9 | 0 |
| 22 | 150 | 99.6 | 0 |
| 23 | 150 | 99.4 | 0 |
| 24 | 150 | 99.4 | 0 |
| 25 | 150 | 96.1 | 0 |
| 26 | 150 | 97.1 | 0 |
| 26 | 150 | 97.1 | 0 |
| 27 | 150 | 62.1 | 0 |
| 28 | 150 | 75.1 | 0 |
| 29 | 150 | 58.5 | 0 |
| 30 | 150 | 58.9 | 0 |
| 31 | 150 | 41.0 | 0 |
| 32 | 150 | 67.7 | 2 |
| 33 | 150 | 54.8 | 1 |
| 34 | 150 | 44.3 | 1 |
| 35 | 150 | 41.0 | 0 |
| 36 | 150 | 67.9 | 0 |
| 37 | 150 | 32.0 | 0 |
| 38 | 50 | 23.4 | 0 |
|  | 100 | 78.0 | 0 |
|  | 200 | 99.3 | 1 |
| 39 | 150 | 97.0 | 0 |
| 40 | 150 | 95.1 | 0 |
| 41 | 150 | 97.6 | 0 |
| 42 | 150 | 98.2 | 0 |
| 43 | 150 | 53.5 | 0 |
| 44 | 150 | 80.5 | 0 |
| 45 | 150 | 33.7 | 0 |
| 46 | 100 | 71.7 | 0 |
|  | 200 | 87.2 | 0 |
| 47 | 12.5 | 75.1 | 0 |
|  | 50 | 98.1 | 1 |
|  | 100 | 100.0 | 2 |
| 48 | 50 | 79.2 | 0 |
| 49 | 12.5 | 73.8 | 0 |
|  | 50 | 96.7 | 0 |
|  | 100 | 100.0 | 2 |
| 50 | 12.5 | 62.4 | 0 |
|  | 50 | 96.1 | 1 |
| 51 | 12.5 | 71.6 | 0 |
|  | 50 | 95.3 | 0 |
|  | 100 | 99.4 | 0 |
| 52 | 50 | 88.4 | 0 |
| *53 | 150 | 11 | 0 |
| 54 | 150 | 21 | 1.5 |
| 55 | 150 | 100 | 3.5 |
| 56 | 150 | 100 | 4 |
| 57 | 150 | 14.5 | 0 |
| 58 | 150 | 11.5 | 1 |
| 59 | 150 | 12.3 | 0 |
| 60 | 150 | 76.4 | 0 |
| 61 | 150 | 27.5 | 0 |
| 62 | 150 | 75.7 | 3 |
| 63 | 150 | 28.2 | 3 |
| 64 | 150 | 69.1 | 0 |
| 65 | 150 | 98.4 | 4 |
| 66 | 150 | 66.8 | 3 |
| 67 | 150 | 78.0 | 4 |

*Examples 53 to 67 were evaluated three weeks after treatment

EXAMPLE 54

Emulsifiable Concentrate Formulations

The following example shows typical emulsifiable concentrate formulations of a compound for use in practicing the invention.

| Formulation I | | |
|---|---|---|
| 3-methyldiphenyl sulfide | 27% | (by weight) |
| octylphenoxypolyethoxyethanol (7.5 mol ethylene oxide) | 23% | |
| water | 50% | |
| Formulation II | | |
| 3-chlorodiphenyl sulfide | 48% | |

| -continued | |
|---|---|
| C$_8$-C$_{10}$ fatty alcohol blend (Alfol 810) | 31% |
| octylphenoxypolyethoxyethanol (7.5 mol ethylene oxide) monohydrogen and dihydrogen phosphate esters | 16% |
| octylphenoxypolyethoxyethanol (30 mol ethylene oxide) | 5% |

It is to be understood that changes and variations may be made without departing from the spirit and scope of the invention as defined by the appended claims.

I claim:

1. A method for controlling the growth of suckers in growing tobacco plants which comprises applying to the plants an effective amount of a compound of the formula

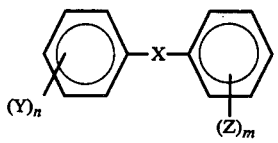

wherein
X is an oxygen atom or a sulfur atom each Y and each Z independently is a halogen atom, a (C$_1$-C$_8$) alkyl group, a trifluoromethyl group, a (C$_1$-C$_4$) alkoxy group, a hydroxy group, a nitro group, a cyano group, a carboxy group, a carb(C$_1$-C$_4$)-alkoxy group, a carbamoyl group, a carb(C$_1$-C$_4$)-alkyl or (C$_1$-C$_4$)-dialkyl carbamoyl group, or a (C$_1$-C$_4$)-alkylthio group,
$m$ is 0, 1,2,3, and
$n$ is 0, 1,2,3.

2. The method of claim 1 wherein X is an oxygen atom.

3. The method of claim 2 wherein $m$ is 0.

4. The method of claim 3 wherein Y is a halogen atom, an alkyl group, an alkoxy group, or a nitro group, and $n$ is 1.

5. The method of claim 4 wherein Y is a chlorine atom.

6. The method of claim 4 wherein Y is a methyl group.

7. The method of claim 2 wherein the compound is applied at a rate of about 0.5 to about 20 pounds per acre.

8. The method of claim 1 wherein X is a sulfur atom.

9. The method of claim 8 wherein $m$ is 0.

10. The method of claim 9 wherein Y is a halogen atom, an alkyl group, an alkoxy group, or a nitro group, and $n$ is 1.

11. The method of claim 10 wherein Y is a chlorine atom.

12. The method of claim 10 wherein Y is a methyl group.

13. The method of claim 8 wherein the compound is applied at a rate of about 0.5 to about 20 pounds per acre.

* * * * *